US012570592B2

(12) United States Patent
Okada et al.

(10) Patent No.: US 12,570,592 B2
(45) Date of Patent: Mar. 10, 2026

(54) HIGHER SECONDARY ALCOHOL ALKOXYLATE PRECURSOR, HIGHER SECONDARY ALCOHOL ALKOXYLATE ADDUCT AND HIGHER SECONDARY ALKYL ETHER SULFATE ESTER SALT, AND METHODS FOR PRODUCING THESE

(71) Applicant: NIPPON SHOKUBAI CO., LTD., Osaka (JP)

(72) Inventors: Atsushi Okada, Kawasaki (JP); Toru Inaoka, Kawasaki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 772 days.

(21) Appl. No.: 17/753,461

(22) PCT Filed: Sep. 8, 2020

(86) PCT No.: PCT/JP2020/033959
§ 371 (c)(1),
(2) Date: Mar. 3, 2022

(87) PCT Pub. No.: WO2021/049492
PCT Pub. Date: Mar. 18, 2021

(65) Prior Publication Data
US 2022/0324781 A1 Oct. 13, 2022

(30) Foreign Application Priority Data

Sep. 9, 2019 (JP) ................................. 2019-164036
Oct. 31, 2019 (JP) ................................. 2019-199188

(51) Int. Cl.
| | |
|---|---|
| C07C 43/13 | (2006.01) |
| C07C 41/03 | (2006.01) |
| C07C 41/06 | (2006.01) |
| C07C 41/38 | (2006.01) |
| C07C 303/24 | (2006.01) |
| C08G 65/26 | (2006.01) |
| C08G 65/329 | (2006.01) |
| C08G 65/334 | (2006.01) |
| C11D 1/29 | (2006.01) |
| C11D 1/72 | (2006.01) |
| C11D 1/83 | (2006.01) |

(52) U.S. Cl.
CPC .............. *C07C 43/13* (2013.01); *C07C 41/03* (2013.01); *C07C 41/06* (2013.01); *C07C 41/38* (2013.01); *C07C 303/24* (2013.01); *C08G 65/2609* (2013.01); *C08G 65/329* (2013.01); *C08G 65/3344* (2013.01); *C11D 1/29* (2013.01); *C11D 1/72* (2013.01); *C11D 1/83* (2013.01)

(58) Field of Classification Search
CPC .................................................. C07C 41/06
See application file for complete search history.

(56) References Cited

U.S. PATENT DOCUMENTS

| | | | |
|---|---|---|---|
| 4,371,716 | A | 2/1983 | Paxson et al. |
| 5,994,595 | A | 11/1999 | Onda et al. |
| 6,017,875 | A | 1/2000 | Kadono et al. |
| 2010/0267844 | A1 | 10/2010 | Varineau et al. |

FOREIGN PATENT DOCUMENTS

| | | |
|---|---|---|
| JP | S57-149263 A | 9/1982 |
| JP | S57-192354 A | 11/1982 |
| JP | S63-39993 A | 2/1988 |
| JP | H10-168014 A | 6/1998 |
| JP | H10-218819 A | 8/1998 |
| JP | H10-251216 A | 9/1998 |
| JP | H11-302212 A | 11/1999 |
| JP | H11-349507 A | 12/1999 |
| JP | H11349611 A | 12/1999 |
| JP | 2003-221593 A | 8/2003 |
| JP | 2006-137872 A | 6/2006 |
| JP | 2007-015940 A | 1/2007 |
| JP | 2011-509334 A | 3/2011 |
| KR | 10-1998-0063872 A | 10/1998 |

OTHER PUBLICATIONS

Machine translation of Patent No. JPS6339993A, Feb. 20, 1988, pp. 1-10 (Year: 1988).*
Decision of Refusal dated Oct. 29, 2024, issued for the corresponding Japanese Patent Application No. 2023-045002, 6 pages, with English translation.
Indonesian Office Action for the corresponding Indonesian application No. P00202201262, dated Mar. 24, 2023, with English translation (6 pages).
Notice of Reasons for Refusal for the corresponding Japanese Patent Application No. 2021-545550, dated Jan. 24, 2023, with English translation (12 pages).
PCT, International Search Report for the corresponding patent application No. PCT/JP2020/033959, Nov. 2, 2020, with English translation.
Second Examination Opinion Notice, dated Jul. 23, 2024, for the corresponding Chinese Patent Application No. 202080057513.X, with English Translation.
Korean Intellectual Property Office, "Request for the Submission of an Opinion", dispatched Mar. 19, 2024, which was issued for the corresponding Korean Patent Application No. 10-2022-7003904, 10 pages.
Korean Intellectual Property Office, English translation of "Request for the Submission of an Opinion", dispatched Mar. 19, 2024, which was issued for the corresponding Korean Patent Application No. 10-2022-7003904, 11 pages.

(Continued)

*Primary Examiner* — Medhanit W Bahta
(74) *Attorney, Agent, or Firm* — LUCAS & MERCANTI, LLP

(57) ABSTRACT

A higher secondary alcohol alkoxylate precursor is obtained by reacting a long-chain olefin with a (poly)alkylene glycol. The precursor has a content of (poly)alkylene glycol of 0.2% by mass or lower with respect to the total mass of the higher secondary alcohol alkoxylate; a higher secondary alcohol alkoxylate adduct which is an alkylene oxide adduct of the higher secondary alcohol alkoxylate precursor; and a higher secondary alkyl ether sulfate ester salt which is a sulfated product of the higher secondary alcohol alkoxylate precursor or the higher secondary alcohol alkoxylate adduct.

10 Claims, No Drawings

(56)　　　　　　References Cited

OTHER PUBLICATIONS

JPO, Japanese Office Action mailed Apr. 30, 2024 for the related Japanese application No. 2023-045002, with English translation, 6 pages.

EPO, Extended European Search Report dated Jul. 14, 2023, issued for the corresponding European patent application No. 20864170.4, 7 pages.

Office Action dated Dec. 9, 2023, issued for the corresponding Chinese Patent Application No. 202080057513.X, with English translation, 14 pages.

Office Action dated Jul. 10, 2024, for the corresponding European Patent Application No. 20864170.4.

Request for the Submission of an Opinion, dated Nov. 26, 2024, issued for the corresponding Korean patent application No. 10-2022-7003904, 15 pages, with English translation.

Office Action, dated Feb. 7, 2025, issued for the corresponding Chinese patent application No. 202080057513.X, 14 pages, with English translation.

Office Action, dated Jan. 16, 2025, issued for the corresponding Indonesian patent application No. P00202201262, 6 pages, with English translation.

Office Action, dated Jun. 19, 2025, which was issued for the corresponding Chinese Patent Application No. 202080057513.X, 14 pages, with English translation.

* cited by examiner

HIGHER SECONDARY ALCOHOL ALKOXYLATE PRECURSOR, HIGHER SECONDARY ALCOHOL ALKOXYLATE ADDUCT AND HIGHER SECONDARY ALKYL ETHER SULFATE ESTER SALT, AND METHODS FOR PRODUCING THESE

CROSS REFERENCE TO RELATED APPLICATION

This Application is a 371 of PCT/JP2020/033959 filed on Sep. 8, 2020 which, in turn, claimed the priority of Japanese Patent Application No. 2019-164036 filed on Sep. 9, 2019 and Japanese Patent Application No. 2019-199188 filed on Oct. 31, 2019, both applications are incorporated herein by reference.

TECHNICAL FIELD

The present invention relates to a higher secondary alcohol alkoxylate precursor, a higher secondary alcohol alkoxylate adduct and a higher secondary alkyl ether sulfate ester salt, and methods for producing these.

BACKGROUND ART

Higher secondary alcohol alkoxylates are used in many applications including surfactants for detergents, inks and the like, and lubricants. Higher secondary alcohol alkoxylates have a low solidifying point (pour point) among other surfactants and are excellent in detergency due to low viscosity and high permeability. Higher secondary alcohol alkoxylates are excellent in thermal stability, low-temperature flowability, lubricity, compatibility, mold releasability and the like, among other lubricants. Thus, they are used in various applications.

As an efficient method for producing a higher secondary alcohol alkoxylate, there is disclosed a method for producing a higher secondary alcohol alkoxylate adduct by reacting an α-olefin as a starting material with a (poly)alkylene glycol to obtain a higher secondary alcohol alkoxylate, and adding an alkylene oxide thereto (for example, Patent Literature 1). There is also disclosed a method for producing a higher secondary alcohol alkoxylate (Patent Literature 2). In this method, the double bond of an α-olefin is internally isomerized in the presence of an acid catalyst to make a mixed olefin having a content of the α-olefin of 50% by weight or lower and a content of internal olefin of 50% by weight or higher, and the mixed olefin is reacted with a (poly)alkylene glycol in the presence of an acid catalyst.

A higher secondary alkyl ether sulfate ester salt obtained by sulfating a higher secondary alcohol alkoxylate or a higher secondary alcohol alkoxylate adduct (for example, Patent Literature 3) is also suitably used for detergents such as kitchen cleansers and shampoos because of its excellent detergency.

In recent years, however, there is a demand for further functional enhancement of detergents, with respect to higher secondary alcohol alkoxylate adducts obtained from higher secondary alcohol alkoxylates as their precursors that are provided using a long-chain olefin as a starting material, or cleanser compositions containing the adducts. Furthermore, the generation of odors, and the generation of white turbidness or separated substances in long-term storage occur in some cases. Thus there is room for improvement.

Also, in higher secondary alkyl ether sulfate ester salts obtained from a higher secondary alcohol alkoxylate or a higher secondary alcohol alkoxylate adduct as their precursors, there is room for improvement in odors and skin irritancy.

CITATION LIST

Patent Literature

Patent Literature 1: Japanese Patent Laid-Open No. 10-168014
Patent Literature 2: Japanese Patent Laid-Open No. 11-302212
Patent Literature 3: Japanese Patent Laid-Open No. 10-251216

SUMMARY OF INVENTION

Technical Problem

Then, an object of the present invention is to provide a higher secondary alcohol alkoxylate adduct (or a composition containing the adduct) generating no odors (or odors significantly reduced) and generating no white turbidness or no separated substances (or those significantly reduced) when used as a surfactant, and a higher secondary alkyl ether sulfate ester salt generating no odors (or odors significantly reduced) and having low skin irritancy when used as a surfactant. Another object is to provide a higher secondary alcohol alkoxylate precursor serving as a precursor of the higher secondary alcohol alkoxylate adduct. Still another object is to provide methods for producing the higher secondary alcohol polyalkoxylate precursor, the adduct thereof and the higher secondary alkyl ether sulfate ester salt.

Solution to Problem

An aspect to solve at least one of the above objects is a higher secondary alcohol alkoxylate precursor having a content of a (poly)alkylene glycol of 0.2% by mass or lower with respect to the total mass of the higher secondary alcohol alkoxylate precursor. Another aspect is a higher secondary alcohol alkoxylate adduct which is an alkylene oxide adduct of the higher secondary alcohol alkoxylate precursor. Still another aspect is a higher secondary alkyl ether sulfate ester salt which is a sulfated product of the higher secondary alcohol alkoxylate precursor and/or the higher secondary alcohol alkoxylate adduct.

Effect of Invention

According to an aspects of the present invention, there can be provided a higher secondary alcohol alkoxylate adduct (or a composition containing the adduct) generating no odors (or odors significantly reduced) and generating no white turbidness or no separated substances (or those significantly reduced) when used as a surfactant, and a higher secondary alkyl ether sulfate ester salt generating no odors (or odors significantly reduced) and having low skin irritancy when used as a surfactant. There can also be provided a higher secondary alcohol alkoxylate precursor serving as a precursor of the higher secondary alcohol alkoxylate adduct. There can further be provided methods for producing the higher secondary alcohol polyalkoxylate precursor, the adduct thereof and the higher secondary alkyl ether sulfate ester salt.

DESCRIPTION OF EMBODIMENTS

Hereinafter, the present invention will be described. Then, the present invention is not limited only to the following embodiments. Unless otherwise specified, operations and measurements of physical properties and the like are carried out under the condition of room temperature (20 to 25° C.). "Mass" and "weight", "parts by mass" and "parts by weight", "% by mass" and "% by weight", and "ppm by mass" and "ppm by weight" are each regarded as having the same meanings.

According to an embodiment of the present invention, a higher secondary alcohol alkoxylate precursor is prepared in which the amount of a (poly)alkylene glycol contained in a higher secondary alcohol alkoxylate is controlled to be not higher than a specific amount, and there are provided a higher secondary alcohol alkoxylate adduct by adding an alkylene oxide to the higher secondary alcohol alkoxylate precursor, and a higher secondary alkyl ether sulfate ester salt which is a sulfated product of the precursor or the higher secondary alcohol alkoxylate adduct.

An embodiment of the present invention is a higher secondary alcohol alkoxylate precursor obtained by reacting a long-chain olefin with a (poly)alkylene glycol, wherein the precursor has a content of the (poly)alkylene glycol of 0.2% by mass or lower with respect to the total mass of the higher secondary alcohol alkoxylate precursor. Further another embodiment of the present invention is a higher secondary alcohol alkoxylate adduct which is an alkylene oxide adduct of the higher secondary alcohol alkoxylate precursor. Further still another embodiment of the present invention is a higher secondary alkyl ether sulfate ester salt which is a sulfated product of the higher secondary alcohol alkoxylate precursor or the higher secondary alcohol alkoxylate adduct.

Further yet another embodiment of the present invention is a method for producing a higher secondary alcohol alkoxylate precursor, the method including a step of adding a (poly)alkylene glycol to a double bond of a long-chain olefin (preferably having 8 to 30 carbon atoms) in the presence of a catalyst to obtain a higher secondary alcohol alkoxylate, and a step of bringing a solvent into contact with the reaction liquid of the higher secondary alcohol alkoxylate or a liquid obtained by distilling the higher secondary alcohol alkoxylate to thereby wash the reaction liquid or the liquid to reach a content of the (poly)alkylene glycol of 0.2% by mass or lower with respect to the total mass of the higher secondary alcohol alkoxylate precursor.

Further, yet another embodiment of the present invention is a method for producing a higher secondary alcohol alkoxylate adduct, the method including adding an alkylene oxide to the higher secondary alcohol alkoxylate precursor in the presence of a catalyst, and yet another embodiment is a method for producing a higher secondary alkyl ether sulfate ester salt, the method including sulfating the higher secondary alcohol alkoxylate precursor or the higher secondary alcohol alkoxylate adduct, and further neutralizing the resultant.

<Higher Secondary Alcohol Alkoxylate Precursor>

An aspect of the present invention is a higher secondary alcohol alkoxylate precursor having a content of a (poly) alkylene glycol of 0.2% by mass or lower with respect to the total mass of the higher secondary alcohol alkoxylate precursor (preferably a higher secondary alcohol ethoxylate precursor).

The higher secondary alcohol alkoxylate precursor having such a constitution can suitably be used as a material for producing a higher secondary alcohol alkoxylate adduct generating no odors (or odors significantly reduced) and generating no white turbidness or no separated substances (or those significantly reduced). According to an embodiment of the present invention, the higher secondary alcohol alkoxylate precursor can suitably be used as a material for producing a higher secondary alcohol alkoxylate adduct, which is a surfactant low in pour point, good in permeability, good in foam breaking and excellent in detergency and emulsifiability.

According to an embodiment of the present invention, the higher secondary alcohol alkoxylate precursor is obtained by reacting a (poly) alkylene glycol with a double bond of a long-chain olefin having 8 to 30 carbon atoms preferably in the presence of a catalyst. The number of carbon atoms of the long-chain olefin is preferably 10 to 20, more preferably 14 to 18 and especially preferably 16 to 18. According to an embodiment of the present invention, the number of carbon atoms of the long-chain olefin is 8 to 30, 9 to 26, 10 to 24, 11 to 22, 12 to 20, 14 to 19, 15 to 18, or 16 to 18.

In the case of using, as the (poly)alkylene glycol to be reacted with the long-chain olefin, for example, a monoalkylene glycol, a dialkylene glycol, a trialkylene glycol or a polyalkylene glycol, a higher secondary alcohol alkoxylate is obtained which has, as a main component, a corresponding higher secondary alcohol monoalkoxylate, higher secondary alcohol dialkoxylate, higher secondary alcohol trialkoxylate or higher secondary alcohol polyalkoxylate.

The obtained product contains, in addition to the main component, a monoalkylene glycol, a dialkylene glycol, a trialkylene glycol or a polyalkylene glycol which remains as it is unreacted or is by-produced. In this context, the product (reaction product) of the long-chain olefin with the (poly) alkylene glycol may be in a form of a composition (mixture). According to an embodiment of the present invention, the product may contain, in addition to the (poly)alkylene glycol as a raw material, a by-produced higher secondary alcohol and the like.

The higher secondary alcohol alkoxylate precursor according to the present invention is characterized in that the content of the (poly)alkylene glycol is low. It is essential that the content (content ratio) (a total content when containing multiple kinds (the same applies herein)) of the (poly) alkylene glycol in the higher secondary alcohol alkoxylate precursor is specifically 0.2% by mass or lower. The (poly) alkylene glycol includes monoalkylene glycols, and multimers thereof such as dialkylene glycols, trialkylene glycols and polyalkylene glycols formed by side reactions. According to an embodiment of the present invention, the (poly) alkylene glycol includes monoethylene glycol, diethylene glycol, triethylene glycol, polyethylene glycol, monopropylene glycol, dipropylene glycol, tripropylene glycol, polypropylene glycol, 1,3-propanediol, 1,2-butanediol, 2,3-butanediol, 1,4-butanediol, 1,6-hexanediol, paraxylene glycol and 1,4-cyclohexanemethanediol. In the present invention, if the content of the (poly)alkylene glycol in the higher secondary alcohol alkoxylate precursor exceeds 0.2% by mass, white turbidness is generated when a higher secondary alcohol alkoxylate adduct, which is an adduct of the higher secondary alcohol alkoxylate precursor, is used for a detergent composition. If the white turbidness becomes more, separated substances are generated in the detergent composition, and the adduct thus cannot sufficiently deliver the performance as a surfactant. Further, components of the turbidness and components of the separated substances adhere on the object to be washed in some cases, which is not preferable. According to an embodiment of the present invention, the (poly)alkylene glycol which is an object desired to be removed may be substances originated from a (poly)alkylene glycol to be reacted with the long-chain olefin having 8 to 30 carbon atoms. According to an embodiment of the present invention, the substances originated from the (poly)alkylene glycol may be unreacted substances or side reaction products of a (poly)alkylene glycol to be reacted with the long-chain olefin having 8 to 30 carbon atoms.

The content of the (poly)alkylene glycol (for example, (poly)ethylene glycol) in the higher secondary alcohol alkoxylate precursor according to the present aspect is preferably 0.1% by mass or lower and more preferably 0.05% by mass or lower. The lower limit value is not especially limited, but the content is, for example, 0.01% by mass or higher. According to an embodiment of the present invention, as for the upper limit, the content of the (poly) alkylene glycol is 0.2% by mass or lower, 0.15% by mass or lower, 0.1% by mass or lower, 0.08% by mass or lower, 0.06% by mass or lower, 0.05% by mass or lower, 0.04% by mass or lower, or 0.03% by mass or lower, with respect to the total mass of the higher secondary alcohol alkoxylate precursor. According to an embodiment of the present invention, as for the lower limit, the content of the (poly)alkylene glycol is 0% by mass (not higher than a detection limit), 0.001% by mass or higher, 0.005% by mass or higher, 0.01% by mass or higher, with respect to the total mass of the higher secondary alcohol alkoxylate precursor, for example.

The content of the main component of the higher secondary alcohol alkoxylate precursor depends on the kind of the long-chain olefin used as a raw material, i.e., an $\alpha$-olefin (referred to also as $\alpha$-position) or an internal olefin (referred to also as inner olefin or inner position), and thus the content of the main component is not especially limited. For example, in the case of using momoethylene glycol as the (poly)alkylene glycol and using an $\alpha$-olefin as the long-chain olefin as a raw material, the content of a higher secondary alcohol monoethoxylate, which is a main component of a product, is usually 60% by mass or higher, preferably 70% by mass or higher and more preferably 80% by mass or higher, with respect to a higher secondary alcohol alkoxylate precursor. In the case of using an internal olefin (in an embodiment, isomer mixture) as a raw material, the content of a higher secondary alcohol monoethoxylate, which is a main component of a product, is 80% by mass or higher, preferably 85% by mass or higher and more preferably 90% by mass or higher, with respect to a higher secondary alcohol alkoxylate precursor. Also, in the case of using diethylene glycol, triethylene glycol or the like, the content of a corresponding main component is similar. Then, in Example 1, the content of a higher secondary alcohol monoethoxylate, which was a main component of a product, was about 98 to 99% by mass. Also in the case of using a mixture of an $\alpha$-olefin and an internal olefin as a raw material, the content of a higher secondary alcohol monoethoxylate is not limited to the above content, and may be 60% by mass or higher, preferably 70% by mass or higher and more preferably 80% by mass or higher, or may be 80% by mass or higher, preferably 85% by mass or higher and more preferably 90% by mass or higher, with respect to a higher secondary alcohol alkoxylate precursor.

According to an embodiment of the present invention, the higher secondary alcohol alkoxylate precursor contains, in addition to the main component, by-produced higher secondary alcohol alkoxylates (hereinafter, referred to also as sub-components). For example, in the case of using ethylene glycol (particularly monoethylene glycol) as a reaction material, the main component is a higher secondary alcohol monoethoxylate, and additionally as sub-components, the higher secondary alcohol alkoxylate precursor contains at least one compound such as a higher secondary alcohol and a higher secondary alcohol diethoxylate, in some cases. In the case of containing a higher secondary alcohol diethoxylate as the main component, the higher secondary alcohol alkoxylate precursor contains, as sub-components, at least one of a higher secondary alcohol, a higher secondary alcohol monoethoxylate and a higher secondary alcohol tetraethoxylate, and the like, in some cases. In the case of containing a higher secondary alcohol triethoxylate as the main component, the higher secondary alcohol alkoxylate precursor contains, as sub-components, at least one of a higher secondary alcohol, a higher secondary alcohol monoethoxylate and a higher secondary alcohol diethoxylate, and the like, in some cases.

In the higher secondary alcohol alkoxylate precursor according to the present invention, the content of the sub-components is an amount obtained by subtracting the total of contents of the above main component and the (poly) alkylene glycol (for example, (poly) ethylene glycol) from the total mass of the higher secondary alcohol alkoxylate precursor.

On the higher secondary alcohol alkoxylate precursor according to the present invention, the contents of the main component and the sub-components (unreacted olefin, polymers thereof and the like) can be measured by a known method such as gas chromatography (GC).

Instrument used: GC-2010 (manufactured by Shimadzu Corp.)

Detector: FID, 350° C. (manufactured by Shimadzu Corp.)

Carrier gas: $N_2$ (constant linear speed mode, 30 cm/s)

Column used: DB-1 (inner diameter: 0.25 mm, length: 60 m, membrane thickness: 0.25 μm, manufactured by Agilent Technologies, Inc.)

Column temperature: 50° C.-20° C./min-300° C. (20 min)

Vaporization chamber temperature: 300° C.

The content (content ratio) of the (poly)alkylene glycol (for example, (poly)ethylene glycols) can also be measured by a known analysis method using liquid chromatography (LC). As the measuring condition of liquid chromatography, the following conditions can be adopted in the present invention. This method was also adopted in Examples; and for example, it was confirmed that the purified secondary dodecanol monoethoxylate (1) of Example 1 contained 0.02% by mass of a (poly)alkylene glycol. It was confirmed that the secondary dodecanol ethoxylate adduct (2) of Example 2 contained 0.03% by mass of a (poly)alkylene glycol. It was confirmed that the aqueous solution of a secondary dodecyl ether sulfate ester salt (1) of Example 9 contained 0.02% by mass of a (poly)alkylene glycol with respect to the total mass of the aqueous solution.

Column used: GF310HQ 150 mm (Shodex), 40° C.

Carrier: pure water 1.0 ml/min

Standard substance: PEG standard product Mw500 (manufactured by GL Science Inc.)

Detector: RI detector (LC-20AD, manufactured by Shimadzu Corp.)

Higher Secondary Alcohol Alkoxylate Adduct

A higher alcohol alkoxylate adduct of an aspect of the present invention is a higher secondary alcohol alkoxylate adduct obtained by using the above higher alcohol alkoxylate precursor as a raw material and adding an alkylene oxide thereto.

The higher secondary alcohol alkoxylate adduct (or a composition containing the adduct) according to the present invention generates no odors (or odors significantly reduced) and generates no white turbidness or no separated substances (or those significantly reduced) when used as a surfactant. According to an embodiment of the present invention, the higher secondary alcohol alkoxylate adduct has a low pour point to be easy in handling, and is good in permeability and excellent in detergency and emulsifiability, and the adduct is thus useful as a surfactant, and can be used as it is as a nonionic surfactant. It is preferable that the content (the total content when containing multiple kinds (the same applies herein)) of the (poly)alkylene glycol (for example, (poly)ethylene glycol) in the higher secondary alcohol alkoxylate adduct be 0.3% by mass or lower. A higher alcohol alkoxylate adduct having a content of the (poly)alkylene glycol (for example, (poly) ethylene glycol) more than 0.3% by mass may generate white turbidness in use for a detergent composition. If the content of the (poly)alkylene glycol is much more, separated substances may be generated in the detergent composition to bring about a risk that the performance of the detergent cannot sufficiently be delivered.

According to an embodiment of the present invention, the content (content ratio) of the (poly)alkylene glycol in the higher alcohol alkoxylate adduct is 0.2% by mass or lower, 0.15% by mass or lower, 0.1% by mass or lower, 0.08% by mass or lower, 0.06% by mass or lower, 0.05% by mass or lower, 0.04% by mass or lower, or 0.03% by mass or lower. According to an embodiment of the present invention, the content (content ratio) of the (poly)alkylene glycol in the higher alcohol alkoxylate adduct is 0% by mass (not higher than a detection limit), 0.001% by mass or higher, 0.005% by mass or higher, or 0.01% by mass or higher, for example.

Higher Secondary Alkyl Ether Sulfate Ester Salt

An aspect of the present invention is a higher secondary alkyl ether sulfate ester salt obtained by sulfating the higher secondary alcohol alkoxylate and/or the higher secondary alcohol polyalkoxylate adduct, and further neutralizing the resultant. An embodiment of the present invention is a higher secondary alkyl ether sulfate ester salt having a content (a total content when containing multiple kinds, (the same applies herein)) of the (poly)alkylene glycol of 0.3% by mass or lower. The higher secondary alkyl ether sulfate ester salt of the present invention can be used as it is as an anionic surfactant.

According to an embodiment of the present invention, the higher secondary alkyl ether sulfate ester salt is low in skin irritancy. According to an embodiment of the present invention, the higher secondary alkyl ether sulfate ester salt is excellent in detergency.

The higher secondary alkyl ether sulfate ester salt of the present invention is preferably a surfactant having at least one characteristic from low viscosity, ease in handling, favorable surface tension, favorable foam breaking, excellent detergency and excellent emulsifiability. The higher secondary alkyl ether sulfate ester salt of the present invention can suitably be used in applications such as liquid cleansers and shampoos, because of its low skin irritancy.

In an embodiment of the present invention, the content of the (poly)alkylene glycol in the higher secondary alkyl ether sulfate ester salt is preferably 0.2% by mass or lower, and more preferably 0.1% by mass or lower, 0.08% by mass or lower, 0.06% by mass or lower, or 0.04% by mass or lower. According to an embodiment of the present invention, for the lower limit, the content of the (poly)alkylene glycol in the higher secondary alkyl ether sulfate ester salt is 0% by mass (not higher than a detection limit), 0.001% by mass or higher, 0.005% by mass or higher, or 0.01% by mass or higher, for example.

Method for Producing a Higher Secondary Alcohol Alkoxylate Precursor

A method for producing a higher secondary alcohol alkoxylate precursor, which is an aspect of the present invention, includes a step of adding a (poly)alkylene glycol to a double bond of a long-chain olefin (for example, having 8 to 30 carbon atoms) in the presence of a catalyst to thereby obtain a (crude) higher secondary alcohol alkoxylate, and a step of bringing a solvent into contact with the (crude) higher secondary alcohol alkoxylate to thereby wash the (crude) higher secondary alcohol alkoxylate to reach a content of the (poly)alkylene glycol of 0.2% by mass or lower with respect to the total mass of the higher secondary alcohol alkoxylate precursor (also referred to as washing step).

Therefore, according to an embodiment of the present invention, there is provided a method for producing a higher secondary alcohol alkoxylate precursor, the method including a step of adding a (poly)alkylene glycol to a double bond of a long-chain olefin having 8 to 30 carbon atoms in the presence of a catalyst to thereby obtain a (crude) higher secondary alcohol alkoxylate, and a step of bringing a solvent into contact with the (crude) higher secondary alcohol alkoxylate to thereby wash the (crude) higher secondary alcohol alkoxylate to reach a content of the (poly) alkylene glycol, which is a resultant product (reaction liquid), of 0.2% by mass or lower with respect to the total mass of the higher secondary alcohol alkoxylate precursor.

The long-chain olefin to be used in the present invention includes preferably hydrocarbons having an ethylenic unsaturated bond and having 8 to 30 carbon atoms, and more preferably acyclic straight-chain hydrocarbons having an ethylenic unsaturated bond and having 10 to 20 carbon atoms. The above-mentioned long-chain olefins (including isomer mixtures described herein) are also suitable. Specific examples of the long-chain olefin include octene, decene, dodecene, tetradecene, hexadecene, heptadecene, octadecene or eicosene. These may be used singly or in the form of a mixture of two or more. As the long-chain olefins, any of those having an unsaturated bond on the α position, those having an unsaturated bond on an inner position and those having unsaturated bonds on both of the α position and inner positions can be used without especial limitation. Of course, two or more of these olefins having unsaturated bonds on different positions can be used together.

When the number of carbon atoms of the long-chain olefin is 8 to 30 in the higher secondary alcohol alkoxylate precursor of the present invention, a higher secondary alcohol alkoxylate adduct which is an alkylene oxide adduct of the precursor can exhibit detergency acceptable for practical use. The number of carbon atoms of the long-chain olefin is preferably 10 to 20 and more preferably 14 to 18, in view of detergency. In the case of desiring to impart especially excellent detergency, the number of carbon atoms of the long-chain olefin is especially preferably 16 to 18. According to an embodiment of the present invention, the number of carbon atoms of the long-chain olefin is 8 to 30, 9 to 26, 10 to 24, 11 to 22, 12 to 20, 14 to 19, 15 to 18, or 16 to 18. According to an embodiment of the present invention, if the number of carbon atoms is smaller than 8, sufficient detergency might not be provided. According to an embodiment of the present invention, the number of carbon atoms is 20 or smaller, in view of improving the production efficiency by shortening the time of vacuum distillation in a distillation step in a production process of the higher secondary alcohol alkoxylate precursor.

Inner olefins are usually thermodynamically more stable than α-olefins. Hence, in the case of using an α-olefin as a raw material, the α-olefin is gradually isomerized to inner olefins during reaction. In the case of desiring to further raise the ratio of inner olefins, an α-olefin may be isomerized to an inner olefin by using a catalyst having a capability of internally isomerizing the double bond structure of the α-olefin. Therefore, according to an embodiment of the present invention, the long-chain olefin (for example, having 8 to 30 carbon atoms) is an isomer mixture. According to an embodiment of the present invention, the long-chain olefin (for example, having 8 to 30 carbon atoms) to be used for production is a product internally isomerized by using a catalyst having the above capability. Here, examples of the catalyst having the above capability and capable of causing internal isomerization include catalysts listed in Table 1 in "Journal of Synthetic Organic Chemistry, Japan", vol. 30, No. 10 (1972), p. 874, and Table 4.4 in "Catalyst Lecture 8: Industrial Catalytic Reaction I" (in Japanese) (Koudansha Ltd., edited by Catalysis Society of Japan, 1985), p. 98, and more specifically include acid catalysts, base catalysts and metal-containing catalysts.

Specific examples of the (poly)alkylene glycol usable in the present aspect include monoethylene glycol, diethylene glycol, triethylene glycol, polyethylene glycol, monopropylene glycol, dipropylene glycol, tripropylene glycol, polypropylene glycol, 1,3-propanediol, 1,2-butanediol, 2,3-butanediol, 1,4-butanediol, 1,6-hexanediol, paraxylene glycol and 1,4-cyclohexanemethanediol, but is, in view of the reactivity, preferably a monoalkylene glycol such as monoethylene glycol and monopropylene glycol. These may be used singly or in the form of a mixture of two or more.

The molar ratio of the (poly)alkylene glycol to the long-chain olefin is not especially limited, but is preferably 0.05 to 20, and more preferably 0.1 to 10, 0.5 to 7, 1 to 5, or 1.5 to 4. In the case where the molar ratio is lower than 0.05, the yield of the higher secondary alcohol alkoxylate (precursor) might decrease. On the other hand, in the case of exceeding 20, a reactor having a large volume may be needed uneconomically, which is not preferable. With regard to the reaction condition when the (poly)alkylene glycol is added to an unsaturated bond of the long-chain olefin, the reaction temperature is usually 50 to 250° C., and preferably 100 to 200° C., or 120 to 175° C. The reaction pressure may be reduced pressure, atmospheric pressure or elevated pressure, but is desirably in the range of atmospheric pressure to 20 kg/cm². In the case where the reaction temperature is lower than 50° C., the reaction rate might be too low. On the other hand, in the case of exceeding 250° C., the polymerization of the long-chain olefin, and the decomposition, the polycondensation or the like of the (poly)alkylene glycol may occur to lower the selectivity, for example, which is not preferable.

The addition of the (poly)alkylene glycol to the long-chain olefin is carried out in the presence of an acid catalyst. The acid catalyst is not especially limited and there can be used known catalysts described in Japanese Patent Laid-Open No. 9-52856, Japanese Patent Laid-Open No. 10-167992, and the like. The catalyst is, for example, strongly acidic ion-exchange resins, crystalline aluminosilicates, or dodecylbenzenesulfonic acid, and is preferably the crystalline aluminosilicates, in view of the reactivity; and among these, BEA type zeolite is desirable. In an embodiment of the present invention, as the catalyst to be used for addition of the (poly)alkylene glycol to the long-chain olefin, the same catalyst as for causing internal isomerization can be used. The amount of the catalyst (for example, acid catalyst) is 1 to 50% by mass, and preferably 2 to 30% by mass, 4 to 20% by mass, or 5 to 15% by mass, with respect to the long-chain olefin. In the case where the amount of the catalyst is smaller than 1% by mass, there is a risk that a sufficient catalytic ability is not attained to fail to promote the addition reaction. On the other hand, an amount exceeding 50% by mass is uneconomical and thus not preferable, since a too much amount added does not bring about any commensurate effect, for example.

In the production of the higher secondary alcohol alkoxylate of the present invention, a reaction liquid containing a higher secondary alcohol alkoxylate obtained by adding the (poly)alkylene glycol to the long-chain olefin contains unreacted (poly)alkylene glycol or (poly)alkylene glycol formed by side reactions, and thus, the production of the higher secondary alcohol alkoxylate of the present invention is characterized in that the reaction liquid is subjected to a step of washing with a solvent to wash off the (poly)alkylene glycol.

The reaction for adding the (poly)alkylene glycol to the long-chain olefin produces water since it is a dehydration reaction, and thus a condensation reaction of the (poly)alkylene glycol may be caused as a side reaction to produce multimers. For example, in the case of using monoethylene glycol as a raw material, multimers are produced, such as diethylene glycol, triethylene glycol, tetraethylene glycol and polyethylene glycol. As the addition reaction of the higher secondary alcohol alkoxylate and the (poly)alkylene glycol progresses, the polymerization of such multimers further proceed to form polyalkylene glycols having high molecular weights. The multimers may become compounds having a similar boiling point as the target higher secondary alcohol alkoxylate, depending on the degree of polymerization, and this makes separation and purification by distillation difficult. Hence, it is preferable to wash the resultant with a solvent to extract and remove the multimers such as polyethylene glycol.

In the washing step, one example of the form of the liquid as the object to be washed is a reaction liquid containing the higher secondary alcohol alkoxylate obtained by adding the (poly)alkylene glycol to the long-chain olefin. In this case, it is preferable to carry out a distillation step after the washing step. Another example of the form of the liquid as the object to be washed is a distillate liquid containing the higher secondary alcohol alkoxylate and obtained by carrying out a distillation step of distilling the reaction liquid before a washing step. Although the higher secondary alcohol alkoxylate reaction liquid obtained by the reaction contains sub-components such as a higher secondary alcohol as described above, the sub-components can efficiently be removed by carrying out the distillation step before or after the washing step.

The condition of the distillation step is not especially limited, and a known method can be used. With regard to the distillation temperature, the temperature of the column top of a distillation column is usually 50 to 300° C., preferably 70 to 300° C. and more preferably 70 to 250° C. The residence time for distillation is usually within 24 hours, preferably within 12 hours and more preferably within 6 hours. The residence time for distillation is preferably 10 min or longer, more preferably 20 min or longer and still more preferably 30 min or longer. The distillation may be carried out under either of atmospheric pressure or reduced pressure, but is preferably under reduced pressure, wherein the degree of reduced pressure is preferably 100 mmHg or lower and more preferably 50 mmHg or lower. The degree of reduced pressure is preferably 0.5 mmHg or higher and more preferably 1 mmHg or higher. In the distillation step, low-boiling point materials and impurities can be extracted, whereby the higher secondary alcohol alkoxylate can be purified. Diether compounds remaining in the column bottom may be recovered and added to the reaction system.

A method for the washing step is not especially limited, but a method is suitable in which a solvent is brought into contact with a higher secondary alcohol alkoxylate product obtained by adding the (poly)alkylene glycol to the double bond of the long-chain olefin (preferably having 8 to 30 carbon atoms) in the presence of a catalyst. According to an embodiment of the present invention, a method is suitable in which a solvent is brought into contact with a reaction liquid of a higher secondary alcohol alkoxylate obtained by adding the (poly)alkylene glycol to the double bond of the long-chain olefin (preferably having 8 to 30 carbon atoms) in the presence of a catalyst, or with a reaction liquid obtained by distilling the higher secondary alcohol alkoxylate. In an embodiment of the present invention, an example of the method of bringing the solvent into contact therewith is the following method: the solvent is added to the reaction liquid (reaction solution); the resultant is sufficiently stirred to dissolve the (poly)alkylene glycol(s) in the solvent layer; thereafter, the resultant mixture is allowed to stand to be separated into the reaction solution and the solvent; and the solvent layer is removed.

The solvent to be used in the washing step is preferably a solvent having a polarity different from that of the higher secondary alcohol alkoxylate (particularly a reaction liquid or distilled and purified liquid of the secondary alcohol alkoxylate) and the like, which are the object to be washed, so that they are to be separated into two layers. Further the solvent is preferably one having low solubility in the reaction liquid or distilled and purified liquid and high capability to dissolve the (poly)alkylene glycols (multimers). The solvent is more preferably one having a large difference in boiling point from the reaction liquid or distilled and purified liquid and being capable of being separated by distillation. The boiling point of the solvent is, for example, 0° C. to 200° C., 20° C. to 180° C., or 40° C. to 150° C. Specifically, the solvent is water, an alcohol having 1 to 3 or having 1 or 2 carbon atoms, such as methanol, or an alkali solution thereof and/or a solution of a salt thereof, and these may also be used in the form of a mixture thereof. A solvent containing water is especially preferable. According to an embodiment of the present invention, the solvent contains 70% by mass or more, 80% by mass or more or 85% by mass or more of water. According to an embodiment of the present invention, the solvent is a neutral aqueous solution of sodium sulfate or the like. The alkali solution is preferably of sodium hydroxide (aqueous solution), potassium hydroxide (aqueous solution), triethanolamine (aqueous solution) or the like.

The condition of the washing step is not especially limited. The temperature of the solvent in washing is preferably 20 to 120° C., and may be 30° C. or higher, 40° C. or higher, or 50° C. or higher, and more preferably 60 to 100° C., and may be 60 to 90° C., or 60 to 80° C. A higher temperature is better, because highly added (poly)alkylene glycol, which causes emulsion white turbidness even in the presence of a minute amount thereof, can efficiently be washed. When the temperature of the solvent (solvent for washing) is too low (for example, lower than 20° C.), the anticipated advantageous effects of the present invention are not attained in some cases.

According to an embodiment of the present invention, the time duration for one-time washing is 1 to 120 min, 3 to 90 min, 5 to 60 min, 10 to 50 min, 15 to 40 min, or 20 to 35 min. When the time duration is too short, the anticipated advantageous effects of the present invention are not attained in some cases.

According to an embodiment of the present invention, the number of times of washing is preferably twice or more and more preferably three or more times. When the number of times of washing is too small, the anticipated advantageous effects of the present invention are not attained in some cases. According to an embodiment of the present invention, the number of times of washing is 10 or less times, or 5 or less times.

According to an embodiment of the present invention, the amount of the solvent (solvent for washing) is 5 to 100% by mass, 5 to 50% by mass, or 10 to 25% by mass, with respect to the higher secondary alcohol alkoxylate-containing liquid (liquid as the object to be washed).

An apparatus to be used in the washing step is not especially limited, and examples thereof include an apparatus, like a mixer-settler, in which mixing is carried out by a stirring device of a washing tank section and separation is carried out by a settler section. An apparatus such as a line mixer or a countercurrent washing column can also be used.

In the production of the higher secondary alcohol alkoxylate of the present invention, since a side reaction occurs in some cases in which diethylene glycol and the like turn to dioxane by an acid catalyst, the dioxane also is preferably removed in the above distillation step or washing step.

In the production of the higher secondary alcohol alkoxylate, the distillation step and the washing step are especially preferably carried out in combination, as described above. The order of the distillation step and the washing step is not especially limited. After the washing step is first carried out, the distillation step may be carried out. Specifically, the "higher secondary alcohol alkoxylate" in the "step of bringing a solvent into contact with the higher secondary alcohol alkoxylate to wash it to reach a content of the (poly)alkylene glycol of 0.2% by mass or lower with respect to the total mass of a higher secondary alcohol alkoxylate precursor" may be the "higher secondary alcohol alkoxylate obtained by adding the (poly)alkylene glycol to the double bond of the long-chain olefin having 8 to 30 carbon atoms in the presence of a catalyst and subjecting the resultant to the distillation step" or the "higher secondary alcohol alkoxylate obtained by adding the (poly)alkylene glycol to the double bond of the long-chain olefin having 8 to carbon atoms in the presence of a catalyst without subjecting the resultant to distillation step". In the latter case, it is preferable to later carry out the distillation step.

Method for Producing a Higher Secondary Alcohol Alkoxylate Adduct

According to an aspect of the present invention, there is provided a method for producing a higher secondary alcohol alkoxylate adduct in which method an alkylene oxide is further added to the higher secondary alcohol alkoxylate precursor in the presence of a catalyst.

The method for producing the higher secondary alcohol alkoxylate adduct of the present invention is not especially limited as long as it is a method capable of adding an alkylene oxide to the higher secondary alcohol alkoxylate precursor. According to an embodiment of the present invention, the method for producing the higher secondary alcohol alkoxylate adduct involves, for example, adding an alkylene oxide to the higher secondary alcohol alkoxylate precursor obtained in the above method for producing a higher secondary alcohol alkoxylate precursor to a suitable molar ratio, and reacting the resultant in the presence of an alkali catalyst, an acid catalyst, a solid acid catalyst such as aluminamagnesia, or a double metal cyanide (DMC) catalyst. One or more alkylene oxides may be used. In the latter case, two or more kinds thereof may be added randomly or may be added in blocks, or may be added in the form of a combination of a random structure and a block structure.

Examples of the alkylene oxide include ethylene oxide, propylene oxide, butylene oxide and styrene oxide. The molar ratio of the alkylene oxide to the higher secondary alcohol alkoxylate precursor is not especially limited, but is preferably 1 to 30, more preferably 2 to 25, and still more preferably 4 to 20, 3 to 18, 4 to 16, or 5 to 12.

With regard to the reaction condition for the addition of the alkylene oxide to the higher secondary alcohol alkoxylate precursor, the reaction temperature is usually 50 to 250° C., and preferably 100 to 200° C., 110 to 180° C., or 120 to 160° C. According to an embodiment of the present invention, the reaction time is 0.5 to 40 hours, 0.5 to 20 hours, or 1 to 10 hours; and the reaction pressure may be either of atmospheric pressure or elevated pressure, but is desirably in the range of atmospheric pressure to 20 kg/cm$^2$ (10 kg/cm$^2$ or lower or 5 kg/cm$^2$ or lower). In the case where the reaction temperature is lower than 50° C., the reaction rate might be low. On the other hand, in the case of exceeding 250° C., the decomposition and the increase in by-products may be caused, which is not preferable.

The alkali catalyst includes hydroxides of elements belonging to alkaline metals or alkaline earth metals, for example, sodium hydroxide, potassium hydroxide, lithium hydroxide, magnesium hydroxide, calcium hydroxide and barium hydroxide. In view of easy availability and the reactivity, the alkali catalyst is preferably sodium hydroxide, potassium hydroxide or the like. These may be powdery or granular, or may be added in the form of an aqueous solution and then dehydrated. The amount of the alkali catalyst (in terms of solid content in the case of the form of an aqueous solution) to be used is 0.01 to 2.0% by mass and preferably 0.02 to 0.5% by mass, with respect to an alkoxylate (higher secondary alcohol alkoxylate precursor) as a raw material.

Method for Producing a Higher Secondary Alkyl Ether Sulfate Ester Salt

According to an aspect of the present invention, there is provided a method for producing a higher secondary alkyl ether sulfate ester salt in which method the higher secondary alcohol alkoxylate precursor and/or the higher secondary alcohol alkoxylate adduct obtained by the above production methods is sulfated and further neutralized.

According to an embodiment of the present invention, the higher secondary alkyl ether sulfate ester can be obtained by sulfating the higher secondary alcohol alkoxylate precursor or the higher secondary alcohol alkoxylate adduct, and further neutralizing the resultant. A method of such sulfation is not especially limited, and a known method can be used, such as a method of sulfation with chlorosulfonic acid or sulfuric anhydride (for example, Japanese Patent Laid-Open No. 10-251216), and a method of a sulfating reaction with a sulfating agent diluted with an inert gas (for example, Japanese Patent Laid-Open No. 2000-128853).

In the case of using chlorosulfonic acid in the sulfation, the sulfation is carried out in a batch system by mixing chlorosulfonic acid in the higher secondary alcohol alkoxylate by a known method, for example, involving dropping chlorosulfonic acid directly or while being accompanied by air or an inert gas such as nitrogen, or utilizing a sulfating apparatus equipped with external circulation with a line mixer by the method described in Japanese Patent Publication No. 1-36823, for example. The dropping time of chlorosulfonic acid is 0.5 to 3 hours, or preferably 1 to 2 hours. The reaction temperature is –20 to 30° C. and especially suitably 0 to 20° C.

In the case of using sulfuric anhydride in the sulfation, a known method, for example, the method described in Japanese Patent Publication No. 51-17538 is suitable; sulfation is suitably carried out in a continuous manner, for example, by using a co-current flow thin film reactor, and allowing the higher secondary alcohol alkoxylate precursor and/or the higher secondary alcohol alkoxylate adduct to flow down in a thin film form and allowing sulfuric anhydride gas diluted with an inert gas such as nitrogen gas to co-currently flow to bring the both into gas/liquid contact. The flow rate of the inert gas is preferably 20 to 70 m/s, or 23 to 50 m/s. The concentration of sulfuric anhydride in the gas is preferably 1 to 10% by volume, or 2 to 6% by volume. The molar ratio of the sulfuric anhydride to the higher secondary alcohol alkoxylate is desirably 0.95 to 1.2. The reaction temperature is –20 to 60° C. and especially desirably 0 to 30° C. (or 10° C. to 20° C.)

In the sulfation step, a higher-quality higher secondary alkyl ether sulfate ester salt is enabled to be produced in a higher yield by using a solvent. Examples of the kind of the solvent to be used include chlorine-containing solvents such as chloroform, carbon tetrachloride, ethyl chloride, ethylene chloride, 1,1,1-trichloroethane and 1,1,1,2-tetrachloroethane, hydrocarbon solvents such as n-pentane, n-hexane, n-heptane and cyclohexane, and etheric solvents such as diethyl ether and isopropyl ether. The concentration of the solvent is desirably 10 to 90% by mass in a reaction solution. With the solvent concentration lower than 10% by mass, use of the solvent might not bring about any effect. With that exceeding 90% by mass, the reaction efficiency may worsen to decrease the yield in some cases, which is not preferable.

In the case of using sulfur trioxide (also called sulfuric anhydride) as the sulfating agent, a higher alcohol ethoxylate as a raw material is allowed to react with sulfur trioxide diluted with an inert gas while controlling the concentration of the sulfating agent in the whole gas within the range of 0.1 to 3% by volume, preferably 0.3 to 1.8% by volume and more preferably 0.4 to 1.2% by volume. By doing so, the yield is improved. As the sulfating agent, sulfur trioxide is suitably used; and as the inert gas, air, nitrogen, carbon dioxide gas, or sulfurous acid gas is used, for example.

A tank or tubular reactor can be used for the sulfating reaction. The reaction can be carried out in a batch manner or a continuous manner. It is preferable that the reaction be carried out while the heat of reaction is removed. For the sulfating reaction, a method for continuously carrying out sulfation by using, as a tank reactor, a two-stage reactor installed with a stirrer can be used, for example. As a tubular reactor (for example, round reaction tube), suitable is an apparatus in which a reaction material is allowed to flow in a thin film state on the tube wall. Further a thin-film reactor can also be used in which sulfur trioxide is fed in the form of a gas co-currently or counter-currently, and is allowed to react. Among these, preferable is the co-current thin-film reactor.

In the co-current thin-film reactor, the average flow rate of the whole gas fed to the reaction zone is 20 to 80 m/s and especially preferably 30 to 60 m/s, in terms of linear velocity. The feed rate of the higher alcohol ethoxylate as a raw material is determined depending on the feed rate of sulfur trioxide and the molar ratio between the higher alcohol ethoxylate and the sulfur trioxide. The molar ratio of sulfur trioxide to the higher alcohol ethoxylate as the raw materials is 0.8 to 1.2, and preferably 0.95 to 1.05. The reaction temperature is in the range of − 20° C. to 80° C. and more preferably 0° C. to 60° C., and may be 3 to 40° C., or 5 to 25° C.

After completion of the reaction, the reaction product is separated from the inert gas containing unreacted sulfur trioxide. The separation can be carried out by a usual method, and a cyclone or the like can usually be used.

After the sulfation, the obtained reaction liquid is neutralized with a basic substance, and in the case of having used a solvent, the solvent is removed, whereby the target higher secondary alkyl ether sulfate ester salt can be obtained.

Bases suitable for the neutralization step are alkaline metal hydroxides, more preferably sodium hydroxide, potassium hydroxide and lithium hydroxide, oxides and hydroxides of alkaline earth metals, more preferably magnesium oxide, magnesium hydroxide, calcium oxide, calcium hydroxide, ammonia, alkanolamines, and more preferably mono-, di- and triethanolamines, and primary, secondary and tertiary alkylamines in which alkyl groups each have 1 to 4 carbon atoms.

Detergent, Emulsifier

According to an aspect of the present invention, there is provided a detergent containing at least one of the higher secondary alcohol alkoxylate adduct and the higher secondary alkyl ether sulfate ester salt. According to an aspect of the present invention, there is provided an emulsifier containing at least one of the higher secondary alcohol alkoxylate adduct and the higher secondary alkyl ether sulfate ester salt.

In an embodiment of the present invention, at least one selected from the group consisting of the higher secondary alcohol alkoxylate precursor, the higher secondary alcohol alkoxylate adduct and the higher secondary alkyl ether sulfate ester salt generates no odors (or odors significantly reduced) and generates no white turbidness or no separated substances (or those significantly reduced), or generates no odors (or odors significantly reduced), or has low skin irritancy. In an embodiment of the present invention, at least one selected from the group consisting of the higher secondary alcohol alkoxylate precursor, the higher secondary alcohol alkoxylate adduct and the higher secondary alkyl ether sulfate ester salt is low in pour point, easy in handling, good in permeability, good in foam breaking, excellent in detergency and emulsifiability, generates no white turbidness or no separated substances, and is low further in skin irritancy.

Because of having at least one preferable characteristic from those described above, use thereof as a detergent or an emulsifier is especially preferable.

Detergent

In the detergent of the present invention, the higher secondary alcohol alkoxylate precursor, the higher secondary alcohol alkoxylate adduct and the higher secondary alkyl ether sulfate ester salt may be used singly, but a conventionally known surfactant for detergents may be used in combination (that is, in the form of a composition). Examples of such a surfactant include anionic surfactants such as alkylbenzenesulfonate salts, alkylsulfate ester salts, α-olefinsulfonate salts, alkylsulfonate salts, aliphatic amidesulfonate salts, dialkylsulfosuccinate salts and alkyl ether sulfate ester salts, cationic surfactants such as alkylamine salts and quaternary ammonium salts, and amphoteric surfactants such as alkylbetaines.

Further, various types of additives used for usual detergents can be added to the detergent of the present invention. Examples of such additives include alkali agents, builders, perfumes, fluorescent brighteners, colorants, foaming agents, foam stabilizers, lustering agents, bactericides, bleaching agents, enzymes, antiseptics, dyes and solvents.

The detergent of the present invention can effectively be used as detergents for clothes, textile products, tableware, containers, sundry goods, foods, products for building maintenance, houses, furniture, automobiles, aircrafts, metal products and the like, and shampoos, body shampoos and the like.

According to an embodiment of the present invention, the content (content ratio) of the higher secondary alcohol alkoxylate adduct in the detergent (composition) is 1 to 70% by mass, 3 to 60% by mass, or 5 to 50% by mass. The detergent preferably has a high concentration thereof in view of storage and transportation, but when it is used for cleaning, the detergent is suitably diluted with a solvent such as water, and used.

Emulsifier

Oily substances for which the emulsifier of the present invention is used are not especially limited, and the emulsifier can be used for mineral oils, animal and vegetable oils, synthetic oils and the like. Examples of the mineral oils include spindle oils, machine oils and liquid paraffin oils. Examples of the animal and vegetable oils include beef tallow, lard, fish oil, whale oil, rapeseed oil, sesame oil, coconut oil, soybean oil, palm oil, *camellia* oil and castor oil.

The emulsifier of the present invention can be used for agrochemicals, metal working fluids, paints, emulsifiers for emulsion polymerization.

As described above, the method for producing the higher secondary alcohol alkoxylate precursor of the present invention has the following feature.

The method is remarkably simple.

The method can easily reduce or remove the (poly) alkylene glycol by washing, with a solvent, a product obtained by adding the (poly)alkylene glycol to the double bond of the long-chain olefin, and can obtain the higher secondary alcohol alkoxylate precursor having a content of the (poly)alkylene glycol of not higher than a specific amount.

The detergent containing the higher secondary alcohol alkoxylate adduct or the higher secondary alkyl ether sulfate ester salt produced by using, as a precursor, a higher secondary alcohol alkoxylate (higher secondary alcohol alkoxylate obtained by purification) having a content of the (poly)alkylene glycol of not higher than a specific amount has at least one characteristic from generating no white turbidness or no separated substances or hardly generating them, low pour point, ease in handling, favorable permeability and excellent detergency.

The higher secondary alkyl ether sulfate ester salt of the present invention is further characterized by having low skin irritancy.

EXAMPLES

Hereinafter, the present invention will be described by way of Examples, but the present invention is not any more limited to these Examples.

Example 1 Synthesis of a Higher Secondary Alcohol Monoethoxylate Precursor

5% by mass of a BEA type zeolite, manufactured by PQ Corp. (trade name: VALFOR CP811 BL-25) was added to 1-dodecene, and the liquid phase was allowed to react at 150° C. for 10 hours to obtain a dodecene isomer mixture (composed of 25% by mol of 1-dodecene and 75% by mol of inner dodecene). 810 g (4.82 mol) of the dodecene isomer mixture, 900 g (14.52 mol) of monoethylene glycol (MEG) and 100 g of the BEA type zeolite, manufactured by PQ Corp. (trade name: VALFOR CP811 BL-25) as a catalyst were placed in a 3,000-ml glass reactor equipped with a stirring blade and a reflux condenser; nitrogen purge was performed for the gas phase portion, and then, the nitrogen atmosphere was held at atmospheric pressure. Then, under stirring at a rotating speed of 600 rpm, the temperature was raised to 150° C. and the resultant was allowed to react at the temperature for 3 hours. Thereafter, the reaction liquid was cooled to room temperature. The dodecene phase as the upper layer was separated. After unreacted dodecene was distilled out, 155 g of a secondary dodecanol monoethoxylate (1) was obtained in the boiling point range of 129 to 131° C. (temperature of the column top of a distillation column, the same applies hereinafter) at a degree of reduced pressure of 2 mmHg.

The secondary dodecanol monoethoxylate (1) contained 0.3% by mass of MEG and multimers of MEG. 155 g of the secondary dodecanol monoethoxylate (1) was added to a separable flask; and the operation was repeated three times, the operation including stirring and washing the secondary dodecanol monoethoxylate (1) with 25 g of water by using a stirring blade at 100 rpm at 70° C. for 30 min and thereafter separating the water layer. The resultant was dehydrated to thereby obtain a purified secondary dodecanol monoethoxylate (1). The content of (poly)ethylene glycol in the ethoxylate was 0.02% by mass.

Example 2 Synthesis of a Secondary Dodecanol Monoethoxylate Adduct 155 g (0.67 mol) of the purified secondary dodecanol monoethoxylate (1) obtained in Example 1, and 0.55 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm²G; the temperature was raised to 150° C.; and thereafter, 217 g (4.93 mol) of ethylene oxide was introduced over 3 hours to the autoclave. After the introduction, the temperature was held further for 1 hour at 150° C. Thereafter, the reaction system was cooled to room temperature; and the internal pressure was purged (that is, nitrogen was released for pressure release) to obtain a secondary dodecanol ethoxylate adduct (1) having 8.4 mol on average of oxyethylene groups. The content of (poly)ethylene glycol in the adduct was 0.03% by mass.

Comparative Example 1

A comparative secondary dodecanol ethoxylate adduct (1) was obtained by the same method as in Example 2, except for using 155 g of the secondary dodecanol monoethoxylate (1) of Example 1 in place of 155 g (0.67 mol) of the purified secondary dodecanol monoethoxylate (1) in Example 2. The content of (poly)ethylene glycol was 0.45% by mass.

Example 3 Synthesis of a Secondary Tetradecanol Monoethoxylate Precursor

5% by mass of a BEA type zeolite, manufactured by PQ Corp. (trade name: VALFOR CP811 BL-25) was added to 1-tetradecene, and the liquid phase was allowed to react at 150° C. for 13 hours to obtain a tetradecene isomer mixture (composed of 6% by mol of 1-tetradecene, 15% by mol of 2-tetradecene, 18% by mol of 3-tetradecene, 20% by mol of 4-tetradecene, 17% by mol of 5-tetradecene and 24% by mol of 6,7-tetradecene). 810 g (4.13 mol) of the tetradecene isomer mixture, 900 g (14.52 mol) of monoethylene glycol (MEG) and 100 g of the BEA type zeolite, manufactured by PQ Corp. (trade name: VALFOR CP811 BL-25) as a catalyst were placed in a 3,000-ml glass reactor equipped with a stirring blade and a reflux condenser; nitrogen purge was performed for the gas phase portion, and then, the nitrogen atmosphere was held at atmospheric pressure. Then, under stirring at a rotating speed of 600 rpm, the temperature was raised to 150° C. and the resultant was allowed to react at the temperature for 3 hours. Thereafter, the reaction liquid was cooled to room temperature. The tetradecene phase as the upper layer was separated. The tetradecene phase contained 103 g of a secondary tetradecanol monoethoxylate (1) and 0.4 g of MEG and MEG multimers. 840 g of the tetradecene phase was added in a separable flask; and the operation was repeated three times, the operation including adding 200 g of a water/MeOH (90/10 in mass ratio) solution to the tetradecene phase, stirred the resultant by using a stirring blade at 100 rpm at 60° C. for 30 min and thereafter separating a water layer. Thereafter, the oil layer was distilled. After unreacted tetradecene was distilled out, 102 g of a purified secondary tetradecanol monoethoxylate (1) was obtained in the boiling point range of 170 to 174° C. at a degree of reduced pressure of 5 mmHg. The content of (poly)ethylene glycol in the ethoxylate was 0.03% by mass.

Example 4 Synthesis of a Secondary Tetradecanol Ethoxylate Adduct 102 g (0.40 mol) of the purified secondary tetradecanol monoethoxylate (1) obtained in Example 3, and 0.4 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm²G; the temperature was raised to 150° C.; and thereafter, 150 g (3.42 mol) of ethylene oxide was introduced over 3 hours to the autoclave. After the introduction, the temperature was held further for 1 hour at 150° C. Thereafter, the reaction system was cooled to room temperature, and the internal pressure was purged, to obtain a secondary tetradecanol ethoxylate adduct (1) having 9.6 mol on average of oxyethylene groups. The content of (poly)ethylene glycol in the secondary tetradecanol ethoxylate adduct (1) was 0.04% by mass.

Comparative Example 2

A comparative secondary tetradecanol ethoxylate adduct (1) was obtained by the same method as in Example 4, except for using 102 g of the secondary tetradecanol monoethoxylate (1) of Example 3 in place of 102 g (0.67 mol) of the purified secondary tetradecanol monoethoxylate (1) in Example 4. The content of (poly)ethylene glycol in the adduct was 0.58% by mass.

Example 5 Synthesis of a Secondary Dodecanol Diethoxylate Precursor 184 g of a secondary dodecanol diethoxylate (1) was obtained by the same method as in Example 1, except for using 1,550 g (14.61 mol) of diethylene glycol (DEG) in place of 900 g (14.52 mol) of monoethylene glycol (MEG) in Example 1, and altering the distillation condition to the boiling point range of 170 to 175° C. at a degree of reduced pressure of 5 mmHg. The secondary dodecanol diethoxylate (1) contained 0.4% by mass of DEG and multimers of DEG. 184 g of the secondary dodecanol diethoxylate (1) was added to a separable flask; and the operation was repeated three times, the operation including stirring and washing the secondary dodecanol diethoxylate (1) with 40 g of a 1-mass % NaOH aqueous solution by using a stirring blade at 100 rpm at 80° C. for 30 min, and thereafter separating the water layer. The resultant was dehydrated to thereby obtain a purified secondary dodecanol diethoxylate (1). The content of (poly)ethylene glycol in the ethoxylate was 0.03% by mass.

Example 6 Synthesis of a Secondary Dodecanol Diethoxylate Adduct 184 g (0.67 mol) of the purified secondary dodecanol diethoxylate (1) obtained in Example 5, and 0.4 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm$^2$G; the temperature was raised to 150° C.; and thereafter, 189 g (4.30 mol) of ethylene oxide was introduced over 3 hours to the autoclave. After the introduction, the temperature was held further for 1 hour at 150° C. Thereafter, the reaction system was cooled to room temperature, and the internal pressure was purged, to obtain a secondary dodecanol ethoxylate adduct (2) having 8.4 mol on average of oxyethylene groups. The content of (poly)ethylene glycol in the adduct was 0.03% by mass.

Comparative Example 3

A comparative secondary dodecanol ethoxylate adduct (2) was obtained by the same method as in Example 6, except for using 184 g of the secondary dodecanol ethoxylate (1) of Example 5 in place of 184 g (0.67 mol) of the purified secondary dodecanol diethoxylate (1) in Example 6. The content of (poly)ethylene glycol in the adduct was 0.53% by mass.

Synthesis of a Higher Secondary Alcohol Triethoxylate

Example 7 Synthesis of a Secondary Dodecanol Triethoxylate Precursor 240 g of a secondary dodecanol triethoxylate (1) was obtained by the same method as in Example 1, except for using 2,500 g (16.67 mol) of triethylene glycol (TEG) in place of 900 g (14.52 mol) of monoethylene glycol (MEG) in Example 1, and altering the distillation condition to the boiling point range of 190 to 195° C. at a degree of reduced pressure of 5 mmHg.

The secondary dodecanol triethoxylate (1) contained 0.5% by mass of TEG and multimers of TEG. 240 g of the secondary dodecanol triethoxylate (1) was added to a separable flask; and the operation was repeated three times, the operation including stirring and washing the secondary dodecanol diethoxylate (1) with 50 g of a 1-mass % sodium sulfate aqueous solution by using a stirring blade at 100 rpm at 80° C. for 30 min, and thereafter separating the water layer. The resultant was dehydrated to thereby obtain a purified secondary dodecanol triethoxylate (1). The content of (poly)ethylene glycol in the ethoxylate was 0.03% by mass.

Synthesis of a Higher Secondary Alcohol Triethoxylate Adduct

Example 8 Synthesis of a Secondary Dodecanol Triethoxylate Adduct 240 g (0.75 mol) of the purified secondary dodecanol triethoxylate (1) obtained in Example 7, and 0.6 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm$^2$G; the temperature was raised to 150° C.; and thereafter, 178 g (4.05 mol) of ethylene oxide was introduced over 3 hours to the autoclave. After the introduction, the temperature was held further for 1 hour at 150° C. Thereafter, the reaction system was cooled to room temperature; and the internal pressure was purged to obtain a secondary dodecanol ethoxylate adduct (3) having 8.4 mol on average of oxyethylene groups. The content of (poly)ethylene glycol in the adduct was 0.06% by mass.

Comparative Example 4

A comparative secondary dodecanol ethoxylate adduct (3) was obtained by the same method as in Example 8, except for using 240 g of the secondary dodecanol triethoxylate (1) of Example 7 in place of 240 g (0.75 mol) of the purified secondary dodecanol triethoxylate (1) in Example 8. The content of (poly)ethylene glycol in the adduct was 0.53% by mass.

Example 9 Synthesis of a Secondary Dodecyl Ether Sulfate Ester Salt

By using a reaction tube having a round tubular reaction zone of 5 mm in inner diameter and 100 cm in length, 155 g (0.67 mol) of the purified secondary dodecanol monoethoxylate (1) obtained in Example 1 was allowed to flow down at a rate of 16.2 g/min in a thin film state along on the inner wall of the reaction tube, through a sump on the upper part of the reaction tube and from a weir provided on the upper part. Simultaneously, sulfuric anhydride diluted with nitrogen gas was allowed to flow in from a nozzle installed on the upper part of the reaction tube. The flow rate of the whole nitrogen gas allowed to flow in the reaction tube was adjusted to 30 m/s, and the concentration of sulfuric anhydride in the whole mixed gas allowed to flow in was adjusted to 4% by volume. The molar ratio between the sulfuric anhydride allowed to flow down and the purified secondary dodecanol monoethoxylate (1) allowed to flow down was adjusted to 1.1. The reaction heat generated by the reaction of the ethoxylate with the sulfuric anhydride was removed by a refrigerant flowing outside the reaction tube and the temperature was held at 15° C. The fluid having gone out from the reaction tube was separated to nitrogen gas and a reaction product by a cyclone. The reaction product was immediately neutralized with a sodium hydroxide aqueous solution to thereby obtain an about 25-mass % aqueous solution of a desired secondary dodecyl ether sulfate ester salt (1). The content of (poly)ethylene glycol in the sulfate ester salt aqueous solution was 0.02% by mass.

Example 10 Synthesis of a Secondary Dodecyl Ether Sulfate Ester Salt 155 g (0.67 mol) of the purified secondary dodecanol monoethoxylate (1) obtained in Example 1, and 0.4 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm²G; the temperature was raised to 150° C.; and thereafter, 62 g (1.41 mol) of ethylene oxide was introduced over 3 hours to the autoclave. After the introduction, the temperature was held further for 1 hour at 150° C. Thereafter, the reaction system was cooled to room temperature; and the internal pressure was purged to obtain a secondary dodecanol ethoxylate adduct having 3.1 mol on average of oxyethylene groups.

217 g (0.67 mol) of the secondary dodecanol ethoxylate adduct was placed in a 500-ml flask, and cooled to 10° C. 86.3 g (0.74 mol) of chlorosulfonic acid was dropped therein over about 1 hour. During the dropping, the liquid temperature was kept at 10 to 15° C. After the chlorosulfonic acid dropping, nitrogen gas was allowed to flow in the reaction liquid to remove by-produced hydrogen chloride gas. Then, with the temperature being kept at 20° C. or lower, the reaction liquid was dropped in a sodium hydroxide solution to be neutralized to thereby obtain an about 25-mass % aqueous solution of a desired secondary dodecyl ether sulfate ester salt (2). The content of (poly)ethylene glycol in the sulfate ester salt aqueous solution was 0.03% by mass.

Comparative Example 5

A comparative secondary dodecyl ether sulfate ester salt (1) was obtained by the same method as in Example 9, except for using 155 g of the secondary dodecanol monoethoxylate (1) of Example 1 in place of 155 g (0.67 mol) of the purified secondary dodecanol monoethoxylate (1) in Example 9. The content of (poly)ethylene glycol in the sulfate ester salt aqueous solution was 0.58% by mass.

Example 11 Test for Storage Stability (Turbidness Test)

For the higher secondary alcohol alkoxylate adducts obtained in Examples 2, 4, 6 and 8 and Comparative Examples 1 to 4, the storage stability was determined.

These results of the determination are shown in the following Table 1.

Method for Determination

The storage stability of the higher secondary alcohol alkoxylate adducts each was evaluated by storing 30 g of the adduct at 25° C. or 0° C. and visually checking the presence/absence of turbidness after one month storage.

| Presence of precipitate | 1 |
| Presence of strong turbidness | 2 |
| Being thinly turbid | 3 |
| Being transparent | 4 |

TABLE 1

| | Example | | | | Comparative Example | | | |
| | 2 | 4 | 6 | 8 | 1 | 2 | 3 | 4 |
| 25° C. | 4 | 4 | 4 | 4 | 1 | 1 | 1 | 1 |
| 0° C. | 4 | 4 | 4 | 4 | 1 | 1 | 1 | 1 |

Example 12

Liquid detergent compositions were prepared by mixing any of the higher secondary alcohol alkoxylate adducts obtained in Examples 2, 4, 6 and 8 and Comparative Examples 1 to 4 with the following detergent materials; and the storage stability (turbidness) and the sensory characteristic (odors) were determined. The results are shown in Table 2.

(1) Method of Determining the Storage Stability (Turbidness)

Detergent compositions were prepared according to Table 2, and stored at 25° C. or 0° C.; the presence/absence of separation and turbidness after 3-month storage was visually checked and evaluated based on the following criteria.

| Presence of separation | 1 |
| Presence of precipitate | 2 |
| Presence of strong turbidness | 3 |
| Being thinly turbid | 4 |
| Being transparent | 5 |

(2) Method of Determining the Sensory Characteristic (Odors)

Detergent compositions were prepared according to Table 2, and the presence/absence of odors was checked based on the following criteria by 5 panelists.

| Unpleasant odor | 1 |
| Slightly unpleasant odor | 2 |
| Not unpleasant but some odor | 3 |
| No odor | 4 |

TABLE 2

| | | Example | | | | Comparative Example | | |
|---|---|---|---|---|---|---|---|---|
| | | 2 | 4 | 6 | 8 | 1 | 2 | 3 | 4 |
| LAS | | 25 | 20 | 25 | 25 | 25 | 20 | 25 | 25 |
| nonion | | 20 | 25 | 20 | 20 | 20 | 25 | 20 | 20 |
| AES | | 15 | 15 | 15 | 15 | 15 | 15 | 15 | 15 |
| fatty acid Na | | 5 | ← | ← | ← | ← | ← | ← | ← |
| EtOH | | 5 | ← | ← | ← | ← | ← | ← | ← |
| diethanolamine | | 3 | ← | ← | ← | ← | ← | ← | ← |
| water | | balance | ← | ← | ← | ← | ← | ← | ← |
| turbidity | 25° C. | 5 | 5 | 5 | 5 | 4 | 3 | 4 | 4 |
| | 0° C. | 5 | 5 | 5 | 5 | 2 | 2 | 2 | 2 |
| odor test | | 3 | 3 | 4 | 4 | 3 | 3 | 4 | 4 |

LAS: sodium linear alkylbenzenesulfonate,
nonion: higher secondary alcohol alkoxylate adduct,
AES: polyoxyethylene alkyl ether sulfate salt,
fatty acid Na: fatty acid sodium salt,
EtOH: ethyl alcohol
* Units of numerical values related to compositions of the liquid detergent compositions are all % by mass.

Example 13 Evaluation of the Skin Irritancy

The higher secondary alkyl ether sulfate ester salts obtained in Example 9 and Comparative Example 5 were evaluated for the skin irritancy. The results are shown in Table 3.

By 3 male and 3 female panelists, 6 panelists in total, an experiment was carried out over 2 days. In the experiment, one hand of each panelist was immersed in a detergent solution having a sample concentration of 1% by mass at a solution temperature of 35° C., and the other hand thereof was immersed in water, for 30 min per one day. The hand (X) immersed in the detergent solution and the hand (Y) immersed in water were compared with each other. The hand chaps state was observed and rating was given to the state based on the following criteria. The skin irritancy of the sample was evaluated by averaging the total of the ratings of the panelists. The results are shown in Table 3.

Hand chaps of X were remarkably less than that of Y−2
Hand chaps of X were slightly less than that of Y−1 Hand chaps of X were nearly equal to that of Y 0
Hand chaps of X were slightly more serious than that of Y+1
Hand chaps of X were remarkably more serious than that of Y+2

TABLE 3

| | Example 9 | Comparative Example 5 |
|---|---|---|
| Skin irritancy | −2 | 0 |

Example 14 Synthesis of a Secondary Hexadecanol Monoethoxylate Precursor

5% by mass of a BEA type zeolite, manufactured by PQ Corp, (trade name: VALFOR CP811 BL-25) was added to 1-hexadecene, and the liquid phase was allowed to react at 150° C. for 10 hours to obtain a hexadecene isomer mixture (composed of 25% by mol of 1-hexadecene and 75% by mol of inner hexadecene). 1,082 g (4.82 mol) of the hexadecene isomer mixture, 900 g (14.52 mol) of monoethylene glycol (MEG) and 100 g of the BEA type zeolite, manufactured by PQ Corp. (trade name: VALFOR CP811 BL-25) as a catalyst were placed in a 3,000-ml glass reactor equipped with a stirring blade and a reflux condenser; nitrogen purge was performed for the gas phase portion, and then, the nitrogen atmosphere was held at atmospheric pressure. Then, under stirring at a rotating speed of 600 rpm, the temperature was raised to 150° C. and the resultant was allowed to react at the temperature for 3 hours. Thereafter, the reaction liquid was cooled to room temperature. The hexadecene phase as the upper layer was separated. After unreacted hexadecane was distilled out, 132 g of a secondary hexadecanol monoethoxylate (1) was obtained in the boiling point range of 134 to 138° C. at a degree of reduced pressure of 1 mmHg.

The secondary hexadecanol monoethoxylate (1) contained 0.3% by mass of MEG and MEG multimers. 132 g of the secondary hexadecanol monoethoxylate (1) was added in a separable flask; and the operation was repeated three times, the operation including stirring and washing the secondary hexadecanol monoethoxylate (1) with 25 g of water by using a stirring blade at 100 rpm at 70° C. for 30 min, and thereafter separating a water layer. The resultant was dehydrated to thereby obtain a purified secondary hexadecanol monoethoxylate (1). The content of (poly)ethylene glycol in the ethoxylate was 0.03% by mass.

Example 15 Synthesis of a Secondary Hexadecanol Ethoxylate Adduct 120 g (0.42 mol) of the purified secondary hexadecanol monoethoxylate (1) obtained in Example 14, and 0.25 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm$^2$G; the temperature was raised to 150° C.; and thereafter, 185 g (4.2 mol) of ethylene oxide was introduced over 3 hours to the autoclave. After the introduction, the temperature was held further for 1 hour at 150° C. Thereafter, the reaction system was cooled to room temperature; and the internal pressure was purged to obtain a secondary hexadecanol ethoxylate adduct (2) having 11.0 mol on average of oxyethylene groups. The content of (poly)ethylene glycol in the adduct was 0.03% by mass.

Comparative Example 6

A comparative secondary hexadecanol ethoxylate adduct (1) was obtained by the same method as in Example 15, except for using 120 g of the secondary hexadecanol monoethoxylate (1) of Example 14 in place of 120 g (0.42 mol) of the purified secondary hexadecanol monoethoxylate (1) in Example 15. The content of (poly)ethylene glycol in the adduct was 0.41% by mass.

Example 16 Synthesis of a Secondary Octadecanol Monoethoxylate Precursor

5% by mass of a BEA type zeolite, manufactured by PQ Corp. (trade name: VALFOR CP811 BL-25) was added to 1-octadecene, and the liquid phase was allowed to react at 150° C. for 10 hours to obtain a octadecene isomer mixture (composed of 25% by mol of 1-octadecene and 75% by mol of inner hexadecene). 1,217 g (4.82 mol) of the octadecene isomer mixture, 900 g (14.52 mol) of monoethylene glycol (MEG) and 100 g of the BEA type zeolite, manufactured by PQ Corp. (trade name: VALFOR CP811 BL-25) as a catalyst were placed in a 3,000-ml glass reactor equipped with a stirring blade and a reflux condenser; nitrogen purge was performed for the gas phase portion, and then, the nitrogen atmosphere was held at atmospheric pressure. Then, under stirring at a rotating speed of 600 rpm, the temperature was raised to 150° C. and the resultant was allowed to react at the temperature for 3 hours. Thereafter, the reaction liquid was cooled to room temperature. The octadecene phase as the upper layer was separated. After unreacted octadecane was distilled out, 143 g of a secondary octadecanol monoethoxylate (1) was obtained in the boiling point range of 165 to 169° C. at a degree of reduced pressure of 1 mmHg.

The secondary octadecanol monoethoxylate (1) contained 0.3% by mass of MEG and MEG multimers. 143 g of the secondary octadecanol monoethoxylate (1) was added in a separable flask; and the operation was repeated three times, the operation including stirring and washing the secondary octadecanol monoethoxylate (1) with 25 g of water by using a stirring blade at 100 rpm at 70° C. for 30 min and thereafter separating the water layer. The resultant was dehydrated to thereby obtain a purified secondary octadecanol monoethoxylate (1). The content of (poly)ethylene glycol in the ethoxylate was 0.04% by mass.

Example 17 Synthesis of a Secondary Octadecanol Ethoxylate Adduct 126 g (0.4 mol) of the purified secondary octadecanol monoethoxylate (1) obtained in Example 16, and 0.25 g of a 49% aqueous solution of sodium hydroxide as a catalyst were placed in a stainless steel autoclave, and dehydrated by nitrogen bubbling under a reduced pressure of 13 kPa at 120° C. for 60 min. After nitrogen purge, the pressure in the reactor was adjusted with nitrogen to 1.0 kg/cm²G; the temperature was raised to 150° C.; and thereafter, 201 g (4.6 mol) of ethylene oxide was introduced over 3 hours to the autoclave. After the introduction, the temperature was held further for 1 hour at 150° C. Thereafter, the reaction system was cooled to room temperature; and the internal pressure was purged to obtain a secondary octadecanol ethoxylate adduct (2) having 12.4 mol on average of oxyethylene groups. The content of (poly)ethylene glycol in the adduct was 0.03% by mass.

Comparative Example 7

A comparative secondary octadecanol ethoxylate adduct (1) was obtained by the same method as in Example 17, except for using 126 g of the secondary octadecanol monoethoxylate (1) of Example 16 in place of 126 g (0.4 mol) of the purified secondary octadecanol monoethoxylate (1) in Example 17. The content of (poly)ethylene glycol in the adduct was 0.40% by mass.

Example 18

By using a reaction tube having a round tubular reaction zone of 5 mm in inner diameter and 100 cm in length, 78 g (0.3 mol) of the purified secondary tetradecanol monoethoxylate (1) obtained in Example 3 was allowed to flow down at a rate of 16.2 g/min in a thin film state along on the inner wall of the reaction tube, through a sump on the upper part of the reaction tube and from a weir provided on the upper part. Simultaneously, sulfuric anhydride diluted with nitrogen gas was allowed to flow in from a nozzle installed on the upper part of the reaction tube. The flow rate of the whole nitrogen gas allowed to flow in the reaction tube was adjusted to 30 m/s, and the concentration of sulfuric anhydride in the whole mixed gas allowed to flow in was adjusted to 4% by volume. The molar ratio between the sulfuric anhydride allowed to flow down and the purified secondary tetradecanol monoethoxylate (1) allowed to flow down was adjusted to 1.1. The reaction heat generated by the reaction of the ethoxylate with the sulfuric anhydride was removed by a refrigerant flowing outside the reaction tube and the temperature was held at 15° C. The fluid having gone out from the reaction tube was separated to nitrogen gas and a reaction product by a cyclone. The reaction product was immediately neutralized with a sodium hydroxide aqueous solution to thereby obtain an about 25-mass % aqueous solution of a desired secondary tetradecyl ether sulfate ester salt (1). The content of (poly)ethylene glycol in the sulfate ester salt aqueous solution was 0.02% by mass.

Comparative Example 8

An about 25-mass % aqueous solution of a comparative secondary tetradecyl ether sulfate ester salt (1) was obtained by the same method as in Example 18, except for using 78 g of the secondary tetradecanol monoethoxylate (1) of Example 3 in place of 78 g of the purified secondary tetradecanol monoethoxylate (1) in Example 18. The content of (poly)ethylene glycol in the sulfate ester salt aqueous solution was 0.55% by mass.

Example 19

By using a reaction tube having a round tubular reaction zone of 5 mm in inner diameter and 100 cm in length, 86 g (0.3 mol) of the purified secondary hexadecanol monoethoxylate (1) obtained in Example 14 was allowed to flow down at a rate of 16.2 g/min in a thin film state along on the inner wall of the reaction tube, through a sump on the upper part of the reaction tube and from a weir provided on the upper part. Simultaneously, sulfuric anhydride diluted with nitrogen gas was allowed to flow in from a nozzle installed on the upper part of the reaction tube. The flow rate of the whole nitrogen gas allowed to flow in the reaction tube was adjusted to 30 m/s, and the concentration of sulfuric anhydride in the whole mixed gas allowed to flow in was adjusted to 4% by volume. The molar ratio between the sulfuric anhydride allowed to flow down and the purified secondary hexadecanol monoethoxylate (1) allowed to flow down was adjusted to 1.1. The reaction heat generated by the reaction of the ethoxylate with the sulfuric anhydride was removed by a refrigerant flowing outside the reaction tube and the temperature was held at 15° C. The fluid having gone out from the reaction tube was separated to nitrogen gas and a reaction product by a cyclone. The reaction product was immediately neutralized with a sodium hydroxide aqueous solution to thereby obtain an about 25-mass % aqueous solution of a desired secondary hexadecyl ether sulfate ester salt (1). The content of (poly)ethylene glycol in the sulfate ester salt aqueous solution was 0.02% by mass.

Comparative Example 9

An about 25-mass % aqueous solution of a comparative secondary hexadecyl ether sulfate ester salt (1) was obtained by the same method as in Example 19, except for using 86 g of the secondary hexadecanol monoethoxylate (1) of Example 14 in place of 86 g of the purified secondary hexadecanol monoethoxylate (1) in Example 19. The content of (poly)ethylene glycol in the sulfate ester salt aqueous solution was 0.52% by mass.

Example 20

By using a reaction tube having a round tubular reaction zone of 5 mm in inner diameter and 100 cm in length, 94 g (0.3 mol) of the purified secondary octadecanol monoethoxylate (1) obtained in Example 16 was allowed to flow down at a rate of 16.2 g/min in a thin film state along on the inner wall of the reaction tube, through a sump on the upper part of the reaction tube and from a weir provided on the upper part. Simultaneously, sulfuric anhydride diluted with nitrogen gas was allowed to flow in from a nozzle installed on the upper part of the reaction tube. The flow rate of the whole nitrogen gas allowed to flow in the reaction tube was adjusted to 30 m/s, and the concentration of sulfuric anhydride in the whole mixed gas allowed to flow in was adjusted to 4% by volume. Then, the molar ratio between the sulfuric anhydride allowed to flow down and the purified secondary octadecanol monoethoxylate (1) allowed to flow down was adjusted to 1.1. The reaction heat generated by the reaction of the ethoxylate with the sulfuric anhydride was removed by a refrigerant flowing outside the reaction tube and the temperature was held at 15° C. The fluid having gone out from the reaction tube was separated to nitrogen gas and a reaction product by a cyclone. The reaction product was immediately neutralized with a sodium hydroxide aqueous solution to thereby obtain an about 25-mass % aqueous solution of a desired secondary octadecyl ether sulfate ester salt (1). The content of (poly)ethylene glycol in the sulfate ester salt aqueous solution was 0.02% by mass.

Comparative Example 10

An about 25-mass % aqueous solution of a comparative secondary octadecyl ether sulfate ester salt (1) was obtained by the same method as in Example 20, except for using 94 g of the secondary octadecanol monoethoxylate (1) of Example 16 in place of 94 g of the purified secondary octadecanol monoethoxylate (1) in Example 20. The content of (poly)ethylene glycol in the sulfate ester salt aqueous solution was 0.58% by mass.

Example 21 Test for Storage Stability (Turbidness Test)

For the higher secondary alcohol alkoxylate adducts obtained in Examples 15 and 17 and Comparative Examples 6 and 7, the storage stability was determined.

The determination was carried out by the same method as described above, and these results of the determination are shown in the following Table 4.

TABLE 4

|  | Example | | Comparative Example | |
|---|---|---|---|---|
|  | 15 | 17 | 6 | 7 |
| 25° C. | 4 | 4 | 1 | 1 |
| 0° C. | 4 | 4 | 1 | 1 |

Example 22

Liquid detergent compositions were prepared by mixing any of the higher secondary alcohol alkoxylate adducts obtained in Examples 15 and 17 and Comparative Examples 6 and 7 with the following detergent materials; and the storage stability (turbidness) and the sensory characteristic (odors) were determined by the same method as described above. The results are shown in Table 5.

TABLE 5

|  | Example | | Comparative Example | |
|---|---|---|---|---|
|  | 15 | 17 | 6 | 7 |
| LAS | 25 | 25 | 25 | 25 |
| nonion | 20 | 25 | 20 | 25 |
| AES | 15 | 15 | 15 | 15 |
| fatty acid Na | 5 |  |  |  |
| EtOH | 5 | ← | ← | ← |
| diethanolamine | 3 | ← | ← | ← |
| water | balance | ← | ← | ← |
| turbidness    25° C. | 5 | 5 | 4 | 3 |
|                       0° C. | 5 | 5 | 2 | 2 |
| odor test | 4 | 4 | 4 | 4 |

*Units of numerical values related to compositions of the liquid detergent compositions are all % by mass.

Example 23 Evaluation of the Detergency

For the higher secondary alcohol ethoxylate adducts obtained in Examples 2, 4, 15 and 17 and Comparative Examples 1, 2, 6 and 7, the detergency was evaluated. The results are shown in Table 6.

Method of Measuring the Detergency

Sebum soil was deposited on a blended yarn fabric of cotton and polyester to obtain soiled cloth, and the soiled cloth was cut into 5 sheets of 5-cm square. The reflectance thereof was measured. After the measurement, the soiled cloth was put in 500 g of a surfactant solution together with 50 g of a white cotton cloth, and washed by using a Tergot-O-Meter (manufactured by Daiei Kagaku Seiki Mfg. Co., Ltd., TM-4) at 120 rpm for 10 min. After the washing, the soiled cloth and the cotton cloth were taken out, and rinsed with 1,000 g of water at 120 rpm for 10 min. After the rinsing, the resultants were dried for one night at room temperature. The reflectance thereof was measured and the detergency ratio was calculated from a change in color difference between before and after the washing. The reflectance was evaluated using a spectrophotometer, SA5500 (manufactured by NIPPON DENSHOKU INDUSTRY, Co., Ltd.).

Soiled cloth: manufactured by wfk-Testgewebe GmbH, WFK 20D

Concentration of the surfactant solution: 0.01% by weight

Water used: pure water (25° C.)

The detergency ratio (detergency) was calculated by using the following expression.

$$\text{Detergency (\%)} = \frac{R_w - R_s}{R_o - R_s} \times 100 \qquad \text{[Expression 1]}$$

In the above expression, $R_o$ represents the reflectance of an original cloth; $R_a$ represents the reflectance of the artificial soiled cloth; and $R_w$ represents the reflectance of the washed cloth.

TABLE 6

| | Example | | | | Comparative Example | | | |
|---|---|---|---|---|---|---|---|---|
| | 2 | 4 | 15 | 17 | 1 | 2 | 6 | 7 |
| Detergency | 16% | 26% | 35% | 36% | 13% | 22% | 29% | 30% |

Example 24 Evaluation of the Detergency

For the higher secondary alkyl ether sulfate ester salts obtained in Examples 9, 18, 19 and 20 and Comparative Examples 5, 8, 9 and 10, the detergency was evaluated. The results are shown in Table 7.

The measurement of the detergency was carried out by the same method as in Example 23, except for making the concentration of the surfactant solution to be 0.03% by weight.

TABLE 7

| | Example | | | | Comparative Example | | | |
|---|---|---|---|---|---|---|---|---|
| | 9 | 18 | 19 | 20 | 5 | 8 | 9 | 10 |
| Detergency | 6% | 33% | 37% | 38% | 5% | 30% | 34% | 35% |

The present application claims to priority to Japanese Patent Application No. 2019-164036, filed on Sep. 9, 2019, and Japanese Patent Application No. 2019-199188, filed on Oct. 31, 2019, the disclosed contents of which are herein incorporated entirely by reference.

The invention claimed is:

1. A method for producing a higher secondary alcohol alkoxylate, the method comprising the steps of:

adding a (poly) alkylene glycol to a double bond of a long-chain olefin having 8 to 30 carbon atoms in the presence of a catalyst to thereby obtain a higher secondary alcohol alkoxylate; and bringing a solvent into contact with the higher secondary alcohol alkoxylate to thereby wash the higher secondary alcohol alkoxylate to reach a content of (poly) alkylene glycol of 0.001% by mass or higher and 0.2% by mass or lower with respect to a total mass of the higher secondary alcohol alkoxylate, wherein the adding is carried out under a solvent-free condition.

2. The method according to claim 1, wherein the solvent is a solvent containing water.

3. A method for producing a higher secondary alcohol alkoxylate adduct, the method comprising further adding an alkylene oxide to the higher secondary alcohol alkoxylate precursor obtained by the method according to claim 1 in the presence of a catalyst.

4. A method for producing a higher secondary alkyl ether sulfate ester salt, the method comprising sulfating the higher secondary alcohol alkoxylate precursor obtained by the method according to claim 1, and further neutralizing the resultant.

5. A method for producing a higher secondary alkyl ether sulfate ester salt, the method comprising sulfating the higher secondary alcohol alkoxylate adduct obtained by the method according to claim 3, further neutralizing the resultant.

6. The method according to claim 1, wherein the higher secondary alcohol alkoxylate is washed to reach the content of (poly) alkylene glycol of 0.005% by mass or higher and 0.2% by mass or lower with respect to the total mass of the higher secondary alcohol alkoxylate.

7. The method according to claim 1, wherein the long-chain olefin comprises an olefin isomer mixture having 12 to 18 carbon atoms.

8. The method according to claim 7, wherein the olefin isomer mixture has 12, 14, 16, or 18 carbon atoms.

9. A method for producing a higher secondary alcohol alkoxylate, the method comprising the steps of:

adding a (poly) alkylene glycol to a double bond of a long- chain olefin having 8 to 30 carbon atoms in the presence of a catalyst only, to thereby obtain a higher secondary alcohol alkoxylate; and bringing a solvent into contact with the higher secondary alcohol alkoxylate to thereby wash the higher secondary alcohol alkoxylate to reach a content of (poly) alkylene glycol of 0.001% by mass or higher and 0.2% by mass or lower with respect to a total mass of the higher secondary alcohol alkoxylate.

10. A method for producing a higher secondary alcohol alkoxylate, the method comprising the steps of:

reacting a (poly) alkylene glycol with a long-chain olefin having 8 to 30 carbon atoms in the presence of a catalyst in a reactor to thereby obtain a higher secondary alcohol alkoxylate, wherein an initial reaction mixture charged to the reactor consists essentially of the long-chain olefin, the (poly) alkylene glycol, and the catalyst; and bringing a solvent into contact with the higher secondary alcohol alkoxylate to thereby wash the higher secondary alcohol alkoxylate to reach a content of (poly) alkylene glycol of 0.001% by mass or higher and 0.2% by mass or lower with respect to a total mass of the higher secondary alcohol alkoxylate.

* * * * *